United States Patent [19]

Steigleder et al.

[11] Patent Number: 5,302,732

[45] Date of Patent: * Apr. 12, 1994

[54] USE OF ULTRA-LOW SODIUM SILICA-ALUMINAS IN THE ALKYLATION OF AROMATICS

[75] Inventors: Karl Z. Steigleder, Glen Ellyn; Christine M. Conway, Rogers Park; David M. Baldwin, Bolingbrook; Diane C. Dierking, Orland Park, all of Ill.

[73] Assignee: UOP, Des Plaines, Ill.

[*] Notice: The portion of the term of this patent subsequent to Mar. 23, 2010 has been disclaimed.

[21] Appl. No.: 944,571

[22] Filed: Sep. 14, 1992

[51] Int. Cl.$^5$ ............ C07C 41/00; C07C 39/12; C07C 2/64; C07C 15/107

[52] U.S. Cl. ............ 554/98; 554/89; 554/97; 252/553; 252/556; 252/558; 562/79; 562/82; 562/88; 562/91; 562/94; 562/95; 562/99; 568/631; 568/632; 568/658; 568/731; 568/732; 568/734; 568/736; 568/766; 568/780; 568/781; 568/785; 568/790; 585/455; 585/456

[58] Field of Search ............ 585/455, 456; 252/553, 252/556, 558; 562/94, 79, 82, 88, 91, 95, 99; 568/631, 632, 658, 731, 732, 734, 736, 766, 780, 781, 785, 790; 554/89, 98

[56] References Cited

U.S. PATENT DOCUMENTS 2,620,314 12/1952 Hoekstra .
3,169,999 2/1965 Erickson et al. .
3,201,487 8/1965 Kovach et al. .
4,301,316 11/1981 Young .................... 585/455
4,301,317 11/1981 Young .................... 585/455
4,358,628 11/1982 Slaugh .................... 585/455
4,870,222 9/1989 Bakas et al. ............. 585/323

FOREIGN PATENT DOCUMENTS 0160145 11/1984 European Pat. Off. .

OTHER PUBLICATIONS

Kurosaki et al, "Effect of Surface Fluorination with $CClF_3$ on Catalytic Activity of $SiO_2$-$Al_2O_3$ for Alkylation of Benzene with Propine", Bull Chem Soc. Japan, 63, 2363 (1990).

Kirosaki et al, "Effect of Surface Treatment with $CHClF_2$ on Catalytic Behavior of $SiO_2$-$Al_2O_3$ and $Al_2O_3$", Chemistry Letters, pp. 589–592 (1991).

R. A. Myers, "Petroleum Refining Processes", 4-36 to 4-38. (McGraw-Hill Book Company), 1986.

Primary Examiner—Patrick P. Garvin
Assistant Examiner—E. D. Irzinski
Attorney, Agent, or Firm—Thomas K. McBride; Eugene I. Snyder

[57] ABSTRACT

Silica-aluminas having a sodium content less than about 0.1 weight percent show increased stability when used as a catalyst for the alkylation of aromatic compounds. Where such silica-aluminas are used as the catalyst in detergent alkylation their increased stability permits continuous alkylation to be performed at lower temperatures, as a result of which the detergent alkylate product shows an incrementally higher linearity. Fluorided silica-aluminas having a sodium content of under 0.05 weight percent are particularly advantageous.

35 Claims, No Drawings

USE OF ULTRA-LOW SODIUM SILICA-ALUMINAS IN THE ALKYLATION OF AROMATICS

BACKGROUND OF THE INVENTION

Over fifty years ago it was recognized that alkylbenzene sulfonates (ABS) were quite effective detergents superior to natural soaps in many respects. Because of their lower price, their price stability, and their effectiveness in a wide range of detergent formulations, ABS rapidly displaced soaps in household laundry and dishwashing applications and became the standard surfactants for the detergent industry.

The alkylbenzene sulfonates had substantial branching in the alkyl chain until the early 1960's when it became apparent that these detergents were contributing to the pollution of lakes and streams and forming relatively stable foams. Examination of the problem showed that alkyl chains with a branched structure were not susceptible to rapid biodegradation and the surfactant properties of the detergent thus persisted for long periods of time. This was contrary to the earlier situation when natural soaps were used because the linear alkyl chains in natural soaps underwent rapid biodegradation.

After recognizing the biodegradability of ABS based on alkylation by linear olefins, industry turned its attention to the production of these unbranched olefins and their subsequent use in the production of linear alkylbenzenes. Processes were developed for efficient alkylation of benzene by available feedstocks containing linear olefins, and the production of linear alkylbenzenes (LABs) became another reliable process broadly available to the petroleum and petrochemical industry. It gradually evolved that HF-catalyzed alkylation was particularly effective in LAB production, and an HF-based alkylation process became the industry standard.

At this point the definition of several terms are necessary to adequately understand and appreciate what follows. Alkylation typically is performed using an excess of benzene relative to olefins. The ideal process would afford 100% conversion of olefins using an equimolar proportion of benzene and olefins, but since this is not attained one strives for maximum olefin conversion using a benzene to olefin molar ratio up to about 30. The better the process, the lower will be the benzene:olefin ratio at a high conversion of, say, 98%. The degree of conversion at a constant value of benzene-olefin ratio is a measure of catalytic activity (subject to the caveat that the ratio must not be so high that the degree of conversion is invariant to small changes in this ratio). The degree of conversion may be expressed by the formula, $$V = \frac{C}{T} \times 100,$$

where V equals percent conversion, C equals moles of olefin consumed, and T equals moles olefin initially present.

However active the catalyst may be, a process based on the catalyst also must be selective. Selectivity is defined as the percentage of total olefin consumed under reaction conditions which appears as monoalkylbenzene and can be expressed by the equation, $$S = \frac{M}{C} \times 100,$$

where S equals selectivity, M equals moles of monoalkylbenzenes produced, and C equals moles olefin consumed. The better the selectivity, the more desirable the process. An approximate measure of selectivity is given by the equation, $$S = \frac{\text{weight monoalkylbenzene}}{\text{weight total products}} \times 100$$

where "total products" includes monoalkylbenzenes, polyalkylbenzenes, and olefin oligomers. At high selectivity (S>85%) the results calculated from the two equations are nearly identical. The latter of the foregoing two equations is routinely used in commercial practice because of the analytical difficulty in distinguishing between oligomers and polyalkylbenzenes.

Finally, the reaction of linear olefins with benzene in principal proceeds according to the equation, $$C_6H_6 + R_1CH=CHR_2 \rightarrow C_6H_5CH(R_1)CH_2R_2 + C_6H_5CH(R_2)CH_2R_1.$$

Note that the side chain is branched solely at the benzylic carbon and contains only one branch in the chain. Although strictly speaking this is not a linear alkylbenzene, nonetheless the terminology which has arisen for the process and product in fact includes as linear alkylbenzenes those materials whose alkyl group chemically arises directly from linear olefins and therefore includes alpha-branched olefins. Because alkylation catalysts also may induce the rearrangement of olefins to ultimately give products which are not readily biodegradable (vide supra), for example, α,α-disubstituted olefins which subsequently react with benzene to afford an alkylbenzene with branching at other than the benzylic carbon, $$R_1CH=CHR_2 \longrightarrow$$

$$R_1CH=C(R_3)R_4 \xrightarrow{C_6H_6} C_6H_5CH(R_1)CH(R_3)R_4$$

the degree to which the catalyst effects formation of linear alkylbenzenes is another important catalyst parameter. The degree of linearity can be expressed by the equation, $$D = \frac{L}{M} \times 100,$$

where D equals degree of linearity, L equals moles of linear monoalkylbenzene produced, and M equals moles of total monoalkylbenzene produced.

Consequently, the ideal process is one where V equals 100, S equals 100, and D equals 100. The minimum requirement is that linearity be at least 90% at a selectivity of at least 85% and at a conversion of at least 99%. These are minimum requirements; that is, if a catalyst fails to meet all of the foregoing requirements simultaneously the catalyst is commercially unacceptable. Moreover, the linearity requirement is assuming added importance and significance in view of the expectation in some areas of minimum standards for linearity in detergents of 92-95% near-term, increasing to 95-98% by about the year 2000. Since the olefinic feedstock used for alkylation generally contains a small percentage of non-linear olefins—a non-linear olefin content of about 2% is common to many processes—the requisite linearity in the detergent alkylate places even more stringent requirements on catalytic performance; the inherent linearity of the alkylation process must increase by the amount of non-linear olefins present in the feedstock. For example, with a feedstock containing 2% non-linear olefins the catalyst must effect alkylation with 92% linearity in order to afford a product with 90% linearity, and with a feedstock containing 4% non-linear olefins the catalyst must effect alkylation with 94% linearity to achieve the same result.

Our solution to the problem of identifying a catalyst for detergent alkylation which satisfies all the aforementioned criteria, and which in particular meets the increasingly stringent requirements of linearity, arose from the observation that the isomerization of linear olefins to non-linear olefins—this is the process ultimately responsible for non-linear detergent alkylate arising from a linear olefin feedstock—is quite sensitive to temperature but relatively insensitive to the particular candidate catalyst for the detergent alkylate process. This result was itself quite surprising, but more importantly it suggested that effecting alkylation at a lower temperature was the key to greater product linearity.

The importance of the observation that temperature is the major factor in olefin isomerization, with the particular catalyst playing only a minor role, cannot be overemphasized, for it permits one to focus solely on methods of reducing the alkylation temperature in order to minimize olefin isomerization and thereby maximize linearity. Since the remaining requisites of a detergent alkylation process can be addressed in other ways, our observation significantly foreshortens the focus on ways to obtain an improved process.

Turning to the object of reducing alkylation temperature, there are two distinct and quite different approaches to achieving this end which we shall refer to as the direct and indirect approaches. The direct approach is to increase catalyst activity. Clearly, as catalyst activity increases—i.e., increasing the rate of reaction of the olefin with benzene at some set of standard reaction conditions—one can lower the alkylation temperature and still attain the requisite conversion and productivity, (the amount of detergent alkylate produced per unit time).

The indirect route of reducing detergent alkylate is to increase catalyst stability. With time, every alkylation catalyst deactivates, and both conversion and productivity decrease to a point where the catalyst must be taken out of service and be regenerated or replaced. The time between regenerations or replacement may be referred to as the lifetime of the catalyst, and the customary solution to a decrease in catalyst stability is to increase operating temperature. The corollary of this is that if an increase in catalyst stability can be effected then the operating temperature may be decreased. To summarize, a consequence of increasing catalyst stability is that one can decrease alkylation temperature without any adverse effects. Since the degree of linearity in linear alkylbenzenes is more highly dependent on the alkylation temperature than on the nature of the alkylation catalyst any process change which permits a lower alkylation temperature leads to an increase in linearity of LABs. It then follows that a consequence of increasing catalyst stability is to produce LABs with a higher linearity because of the reduction in alkylation temperature made possible by the increased catalyst stability.

What we have found is that silica-aluminas having an ultra-low sodium content are considerably more stable than silica-aluminas with a more "normal" sodium content. Typically, silica-aluminas have a sodium content of at least 0.1 weight percent with sodium typically being in the range of 0.1-0.3 weight percent or more. The ultra-low silica-aluminas of this invention have a sodium content of less than 0.1 weight percent. The stability increase attending an ultra-low sodium content is manifested not only by the usual silica-aluminas, but also is manifested by fluorided silica-aluminas.

The use of silica-aluminas as a support for various metals in the alkylation of aromatics with olefins is reasonably well known. For example, U.S. Pat. No. 3,169,999 teaches a catalyst consisting essentially of small amounts of nickel and chromia on a silica-alumina support, and U.S. Pat. No. 3,201,487 teaches 25-50 weight percent chromia on a silica-alumina support, both for alkylation of aromatics by olefins. Crystalline alumina-silicates as catalysts in detergent alkylation has been described in U.S. Pat. Nos. 4,301,317 and 4,301,316. U.S. Pat. No. 4,358,628 claims an alkylation process with an olefin using as a catalyst tungsten oxide supported on a porous silica-alumina support containing 70-90% silica prepared in a very particular way.

More relevant is European Patent Application 0160145 which teaches as a catalyst in detergent alkylation an amorphous silica-alumina having specified channels or networks of pores and with at least 10% of the cationic sites occupied by ions other than alkali or alkaline earth metals. An even more relevant teaching appears in U.S. Pat. No. 4,870,222 where the patentees teach a process for the production of a monoalkylated aromatic compound in which an aromatic is first alkylated, the product mixture is separated, and the polyalkylated material thereafter is transalkylated, and where the most preferred catalyst for alkylation is an amorphous, silica-alumina material, particularly a cogelled silica-alumina prepared as spheroidal particles by the oil drop method.

SUMMARY OF THE INVENTION

A purpose of this invention is to effect the alkylation of benzene with linear olefins using as a catalyst a silica-alumina having an ultra-low sodium content, particularly in a continuous manner, where alkylation proceeds with at least 98% conversion of the olefin, at least 85% selectivity of olefin conversion to monoalkylbenzene, and with at least 90% linearity with respect to monoalkylbenzene formation. In an embodiment the silica-aluminas have a sodium content of less than 0.1 weight percent. In another embodiment the silica-aluminas used as catalysts have a ratio from 1:1 up to about 19:1 of silica:alumina. In yet another specific embodiment the silica-aluminas are fluorided and have a fluorine content from about 1 to about 6 weight percent. In still another specific embodiment the linear olefins have from 6 up to about 20 carbon atoms.

A more general purpose of our invention is to bring about the alkylation of alkylatable aromatic compounds with an alkylating agent in the presence of a silica-alumina having an ultra-low sodium content. In a specific embodiment of this branch of our invention the silica-aluminas contain less than about 0.1 weight percent sodium. In another embodiment the alkylating agent is an olefin which contains from 1 up to about 20 carbon atoms. In yet another embodiment the alkylating agent is an alcohol containing from 1 up to about 20 carbon atoms. In still another embodiment the alkylatable aromatic compound is benzene or an alkyl benzene where the alkyl moiety contains up to about 20 carbon atoms. In a more specific embodiment the alkylatable aromatic compound is a hydroxy benzene. Other purposes and embodiments will become apparent from the ensuing description.

DETAILED DESCRIPTION OF THE INVENTION

What we have observed in the continuous alkylation of benzene with olefins is that silica-aluminas having an ultra-low sodium content show increased stability, that is, have less of a tendency to deactivate and therefore have a longer catalyst lifetime than a silica-alumina with a more "normal" sodium content. For the purpose of this application a silica-alumina with an ultra-low sodium content is defined as one having less than 0.1 weight percent sodium. That such silica-aluminas deactivate slower than those with a sodium content of 0.1 weight percent and more makes it possible to use it as a catalyst in a continuous alkylation process at a substantially lower temperature than that for a silica-alumina with a higher sodium content. Such a decrease in alkylation temperature leads to increased linearity in the preparation of detergent alkylates, as described above, but also helps to avoid side reactions with other alkylatable aromatic substrates and other alkylating agents. Our invention is particularly relevant to detergent alkylation, and we therefore place a heavy emphasis on this aspect of our invention. However, it needs to be clearly understood that our invention is generally applicable to the alkylation of alkylatable aromatic compounds with a large universe of alkylating agents, as will be clear from the material within.

The feedstocks containing the alkylating agent which are used in the practice of that branch of our invention applicable to detergent alkylation normally result from the dehydrogenation of paraffins. Since the entire dehydrogenation reaction mixture often is used, the reaction is not run to completion to minimize cracking, isomerization, and other undesirable and deleterious by-products. The branched olefins which are formed are not removed, yet the total amount of nonlinear alkylbenzene formed still must be sufficiently small that the monoalkylate meets the requirements of 90% linearity. The polyolefins formed during dehydrogenation are minimized in the feedstocks used in the practice of this invention. Consequently the feedstocks are largely a mixture of unreacted paraffins and unbranched, linear monoolefins which typically are in the C6–C20 range, although those in the C8–C16 range are preferred in the practice of this invention, and those in the C10–C14 range are even more preferred. Unsaturation may appear anywhere on the linear monoolefin chain; there is no requirement as to the position of the double bond, but only a requirement as to the linearity of the olefin. See R. A. Myers, "Petroleum Refining Processes", 4-36 to 4-38. (McGraw-Hill Book Company), 1986.

In the broader case the alkylating agent is an olefin, an alcohol, or an alkyl halide containing from 1 up to about 20 carbon atoms. Where the alkylating agent is an olefin the latter may be either branched or unbranched and also may be substituted with, for example, an aromatic substituent. Examples of suitable olefins include ethylene, propylene, butene, pentene, hexene, heptene, octene, nonene, decene, undecene, dodecene, tridecene, tetradecene, pentadecene, hexadecene, heptadecene, octadecene, nonadecene, and eicosene. Further examples include styrene, phenylpropene, phenylbutene, phenylpentene, phenylhexene, and so forth.

Another class of alkylating agents which may be used in the practice of our invention are alcohols. Like the olefins, the alkyl chain in the alcohol may be branched or unbranched and the hydroxyl group may be found anywhere on the alkyl chain. That is, there is no particular requirement as to the spatial position of the hydroxyl moiety on the alkene chain. Examples of alcohols which may be successfully used in our invention include methanol, ethanol, propanol, butanol, pentanol, hexanol, heptanol, octanol, nonanol, decanol, undecanol, tetradecanol, and so forth. Especially relevant to this branch of the invention is methanol as the alcohol.

The last of the three classes of alkylating agents which may be frequently used in the practice of this invention are alkyl halides. Alkyl chlorides are probably the most widely used alkyl halides, but alkyl bromides also may be successfully used in the practice of our invention. As with alcohols, the paraffinic chain may be either branched or unbranched and the halogen may be found at any position along the chain. Suitable examples of alkyl halides include propyl chloride, propyl bromide, butyl chloride, butyl bromide, pentyl chloride, pentyl bromide, hexyl chloride, hexyl bromide, heptyl chloride, heptyl bromide, benzyl chloride, benzyl bromide, xylyl chloride, xylyl bromide, phenethyl chloride, phenethyl bromide, allyl chloride, allyl bromide, butenyl chloride, butenyl bromide, and so forth.

Where the process is detergent alkylation, the linear monoolefins in the feedstock are reacted with benzene. Although the stoichiometry of the alkylation reaction requires only 1 molar proportion of benzene per mole of total linear monoolefins, the use of a 1:1 mole proportion results in excessive olefin polymerization and polyalkylation. That is, the reaction product under such conditions would consist of not only the desired monoalkylbenzenes, but would also contain large amounts of the dialkylbenzenes, trialkylbenzenes, possibly higher polyalkylated benzenes, olefin dimers, trimers, etc., and unreacted benzene. On the other hand, it is desired to have the benzene:olefin molar ratio as close to 1:1 as possible to maximize benzene utilization and to minimize the recycle of unreacted benzene. The actual molar proportion of benzene to total monoolefins will therefore have an important effect on both conversion and, perhaps more importantly, selectivity of the alkylation reaction. In order to carry out alkylation with the conversion, selectivity, and linearity required using the catalysts of our process, a total benzene:linear monoolefin molar ratio of from 5:1 up to as high as 30:1 is recommended, although the process normally operates satisfactorily at a total benzene:linear monoolefins molar ratio between about 8:1 and about 20:1.

In the more general case the alkylating agent is reacted with an alkylatable aromatic compound. Such aromatic compounds are selected from the group consisting of benzene, naphthalene, anthracene, phenanthracene, and substituted derivatives thereof. The most important class of substituents are alkyl moieties containing from 1 up to about 20 carbon atoms. Another important substituent is the hydroxyl moiety as well as the alkoxy moiety whose alkyl group also contains from 1 up to 20 carbon atoms. Where the substituent is an alkyl or alkoxy group, a phenyl moiety also can be substituted on the paraffinic chain. Although unsubstituted and monosubstituted benzenes, naphthalenes, anthracenes, and phenanthrenes are most often used in the practice of this invention, polysubstituted aromatics also may be employed. Examples of suitable alkylatable aromatic compounds include benzene, naphthalene, anthracene, phenanthrene, biphenyl, toluene, xylene, ethylbenzene, phenol, anisole, propylbenzene, butylbenzene, pentylbenzene, hexylbenzene, heptylbenzene, octylbenzene, and so forth; anisole, ethoxy-, propoxy-, butoxy-, pentoxy-, hexoxybenzene, and so forth.

Where the process is detergent alkylation, the benzene and linear monoolefins in the $C_6$–$C_{20}$ range, are reacted in the presence of a catalyst under alkylation conditions. These alkylation conditions include a temperature in the range between about 60° C. and 175° C., most usually between about 70° C. and 150° C., and preferably in the range from 80° to 135° C. Since the alkylation is conducted as a liquid phase process, pressures must be sufficient to maintain the reactants in the liquid state. The requisite pressure necessarily depends upon the feedstock and temperature, but normally is in the range of 200–1000 psig, and most usually 300–500 psig.

In the more general case, there is a wide variation in the alkylation conditions of an alkylatable aromatic compound by an alkylating agent depending upon the reactivity of the two reactants. For example, for hydroxy benzenes (phenols) the hydroxyl moiety is found to be a quite activating group toward alkylation, and therefore the hydroxy benzenes are readily alkylated so that temperatures of no more than about 150° C. suffice. On the other hand, where the aromatic is an unsubstituted aromatic, such as benzene, and the alkylating agent is a lower olefin, such as propylene, temperatures as high as 400° C. may be necessary. Consequently, the temperature range appropriate for alkylation will be between about 60° and about 400° C., with the most usual temperature range being between 100° and 225° C. As regards pressures, since the alkylation is desirably conducted as a liquid phase process the reaction pressure must be sufficient to maintain the reactants in the liquid stage. This is the sole pressure requirement for the practice of this invention, and since a wide variety of alkylatable aromatics compounds and alkylating agents may be used in the practice of this invention it can be readily appreciated that there exists a wide variation in reaction pressure, from atmospheric up to as high as about 2000 pounds per square inch.

The alkylation of benzene by linear monoolefins with the requisite conversion, selectivity, and linearity, and of other aromatic substrates by the alkylating agents of our invention, is effected by silica-aluminas containing a weight ratio of silica to alumina of at least 1:1 up to as high as 19:1. Those silica-aluminas with a silica:alumina ratio of 2:1 (67:33) up to about 19:1 (ca. 95:5) are preferred in the practice of this invention. An amorphous, cogelled, oil-dropped silica-alumina is preferred for the successful practice of this invention. The oil-drop method of preparing, for example, aluminas is an old, tried and true method dating to U.S. Pat. No. 2,620,314, and therefore will not here be discussed in great detail. The following description will be familiar to one practicing this art and will serve as a general description of the subject method.

The cogelled silica-alumina composition is suitably prepared as spheroidal particles by the well-known oil-drop method. In a preferred method of manufacture, an alumina sol, utilized as an alumina source, is commingled with an acidified water glass (sodium silicate) solution as a silica source, and the mixture is further commingled with a suitable gelling agent, for example, urea, hexamethylenetetraamine (HMT), or mixtures thereof. The mixture is discharged while still below gelation temperature by means of a nozzle or rotating disk into a hot oil bath maintained at or above gelation temperature. The mixture is dispersed into the hot oil bath as droplets which form into spherical gel particles. The alumina sol is preferably prepared by a method wherein aluminum pellets are commingled with a quantity of treated or deionized water, with hydrochloric acid being added thereto in a sufficient amount to digest a portion of the aluminum metal and form the desired sol. A suitable reaction rate is effected at about reflux temperature of the mixture.

The spheroidal gel particles prepared by the oil-drop method are atmospherically aged, usually in the oil bath, for a period of 6–16 hours, and then washed, preferably with an aqueous ammonia-ammonium nitrate solution, in a suitable alkaline or basic medium for at least 3 to about 10 hours, and finally water rinsed. Proper gelation of the mixture in the oil bath, as well as subsequent aging of the gel spheres, is not readily accomplished below about 50° C., and at about 100°–110° C. the rapid evolution of the gases tend to rupture and otherwise weaken the spheres. Pressure aging, although not usually performed, is a possible option. By maintaining sufficient superatmospheric pressure during the forming and aging steps in order to maintain water in the liquid phase, a higher aging temperature may be employed, perhaps with improved results.

The spheres are water-washed, preferably with water containing a small amount of ammonium hydroxide and/or ammonium nitrate. After washing, the spheres are dried, at a temperature from about 85°–300° C. for a period from about 6 to about 24 hours or more, and then calcined at a temperature from about 300°–760° C. for a period from about 2 to about 12 hours or more.

Fluorided silica-alumina catalysts also have been found to be effective in the practice of this invention and are prepared by impregnating the silica-alumina with essentially hydrogen fluoride. This is not to say that HF is the only fluoride source, but rather that the fluoride source is equivalent to HF in affording a fluorided silica-alumina free of additional metals or metallic species and which analytically contains only additional HF. Examples of a suitable fluoride source, in addition to HF, include ammonium fluoride [$NH_4F$], ammonium bifluoride [$NH_4HF_2$], and organic fluorides. When an ammonium fluoride is used $NH_3$ is volatilized during subsequent heating of the fluoride-impregnated silica-alumina. When organic fluorides are used the impregnated silica-alumina is subsequently heated under conditions which oxidize carbon to carbon dioxide and excess hydrogen to water, both of which volatilize to leave the equivalent of an HF-impregnated product.

The preparation of the fluorided silica-alumina catalyst may be performed by a variety of procedures, depending upon the fluoride source, fluoride level sought, and so forth. For example, when an ammonium fluoride is used equal volumes of the silica-alumina and an aqueous solution of the ammonium fluoride containing the desired amount of fluoride are intimately mixed, (e.g., cold rolled) and the mixture subsequently heated to evaporate the water. The resulting fluoride-impregnated product may be dried at 125°–175° C. for several hours, and then calcined at a temperature typically in the 350°–550° C. range for 1–6 hours, depending on the temperature used. For calcination near 400° C. the time generally is about 3 hours. It is found that ammonia is lost from the catalyst when the impregnated material is heated to about 150° C. Small amounts of fluoride are lost up to a temperature of about 550° C., but greater fluoride loss is observed at higher temperatures.

When HF is the fluoride source a similar impregnation method may be used, although it also is possible to fluoride the catalyst with a gaseous HF stream. In the latter instance no drying step is necessary and the fluorided material may be calcined directly. Where an organic fluoride is used, the silica-alumina may be impregnated using either a vapor phase or liquid phase source of fluoride. For example, an organic fluoride such as t-butyl fluoride can be impregnated from its solution in a volatile solvent, the solvent subsequently removed by evaporation, the silica-alumina heated to remove the last traces of solvent and then calcined to remove the organic material. This procedure is similar to impregnation using inorganic fluoride but may suffer from fluoride loss on calcination. Alternatively, the t-butyl fluoride may be volatilized, and HF deposited on the silica-alumina via thermal decomposition of the t-butyl fluoride. Fluoride levels can be controlled by gas rate, time and temperature of exposure.

The foregoing procedures for making a fluorided silica-alumina are not unique. Others may be employed as a matter of choice by the skilled artisan.

Where fluorided silica-aluminas are utilized as catalysts the fluoride, expressed as fluorine, is present at levels from about 1 up to as high as about 6 weight percent. Although more highly fluorided silica-aluminas may be used as catalysts no further incremental benefits appear to accrue. In the most usual case fluorine is present at levels from about 1.5 up to about 3.5 weight percent.

The key to our invention is the use of silica-aluminas having an ultra-low sodium content. Sodium content must be less than about 0.1 weight percent, although it is preferred to use silica-aluminas, whether or not fluorided, with a sodium content no more than about 0.05 weight percent, and it is still more highly preferred to use silica-aluminas with a sodium content no more than about 0.03 weight percent. When such silica-aluminas are utilized as catalysts in the practice of our invention it is observed that catalyst lifetime is substantially increased to the point where lower alkylation temperatures may be easily employed without any detrimental or disadvantageous results while retaining a reasonable catalyst life.

The ultra-low sodium silica-aluminas of our invention may be readily prepared by several methods. One method is to wash the oil-aged spheres well with aqueous ammonium hydroxide-ammonium nitrate so that a low sodium concentration is reached in the calcined base. Standard chemical and engineering techniques (such as having sufficient ammonium hydroxide and ammonium nitrate, high linear velocity of the wash solution, and an adequate volume of wash water for the volume of spheres treated) are used to ensure efficient washing.

Another method is to wash the calcined base to remove sodium. This approach is similar to removing sodium from a zeolite or to any other cation exchange process where $H^+$ or $NH_4^+$ is exchanged for an alkali or alkaline earth metal cation. The aqueous wash solution may contain HCl, $NH_4NO_3$, $NH_4Cl$, $HNO_3$, $(NH_4)N_3$, for example, and exchange may be accomplished by cycling the wash solution through a packed bed of the calcined base followed by a water rinse using techniques well known to the skilled worker.

Although the first described method is, at least in theory, the preferred choice, the actual method used will depend, for example, on available equipment, the particular physical properties sought in the final preparation, extraneous manufacturing considerations, and so on.

In one preferred mode the silica-alumina catalysts of our invention are employed as spheres in a packed bed. As an adjunct to the increased stability manifested by the ultra-low sodium silica-aluminas, we have found that sphere size also can appreciably affect catalyst life. In particular, spherical particles no more than about one-sixteenth inch in diameter have a substantially beneficial ancillary effect, and spherical particles with a diameter of less than 1/16 inch are even more highly desirable. In a variant of our invention we have used spherical particles with a diameter no more than about 1/32 inch and have obtained substantial incremental benefits in catalyst stability permitting a further decrease in alkylation temperature.

Alkylation of benzene by linear monoolefins according to this invention may be conducted either in a batch method or in a continuous manner, although the latter is greatly preferred and therefore will be described in some detail. The ultra-low sodium silica-alumina catalyst may be used as a packed bed, ebullating bed, or a fluidized bed. Feedstock to the reaction zone may be passed either upflow or downflow, or even horizontally as in a radial bed reactor. The admixture of benzene and the feedstock containing the total linear monoolefins is introduced at a total benzene:olefin ratio of between 5:1 and 30:1, although usually the ratio is in the range between about 8:1 and 20:1. In one desirable variant olefin may be fed into several discrete points within the reaction zone, and at each zone the benzene:olefin ratio may be greater than 30:1. However, the total benzene:olefin ratio used in the foregoing variant of our invention will still be within the stated range. The total feed mixture, that is, benzene plus feedstock containing linear monoolefins, is passed through the packed bed at a liquid hourly space velocity (LHSV) between about 0.3 and about 6 $hr^{-1}$ depending upon alkylation temperature, how long the catalyst has been used, the ratio of silica to alumina in the catalyst, its sodium content, whether it has been fluorided, and so on. The temperature in the reaction zone for detergent alkylation will be maintained at between about 60° and about 175° C., but more often between 70° and 150° C., and most often in the range of 80° to 135° C., and pressures will generally vary between about 200 and about 1000 psig to ensure a liquid phase alkylation. After passage of the benzene and linear monoolefin feedstock through the reaction zone, the effluent is collected and separated into benzene, which is recycled to the feed end of the reaction zone, paraffin, which is recycled to the dehydrogenation unit, and alkylated benzenes. The alkylated benzenes are usually further separated into the monoalkyl benzenes, used in subsequent sulfonation to prepare the linear alkylbenzene sulfonates, and the oligomers plus polyalkylbenzenes. Since the reaction goes to at least 98% conversion, little unreacted monoolefin is recycled with paraffin.

For alkylation other than detergent alkylation, i.e., in the more general case, the reaction between the alkylatable aromatic compound in the alkylating agent will generally take place as described above. Whether the aromatic or the alkylating agent is used in excess depends upon the relative economics of the process, the desirability of the predominance of a particular product, the tendency toward oligomerization of, for example, the olefin, and so forth. However, in general the ratio of the alkylatable aromatic substrate and alkylating agent may range between about 1:20 and 20:1. As stated previously, alkylation temperatures will be in the range of 60°–400° C., although temperatures between 100° and 225° C. are more the norm. Pressures will be adequate to ensure a liquid phase alkylation and usually will be no more than about 500 pounds per square inch, although in the case of lower olefins higher temperatures up to perhaps 2,000 psig may be employed. Whether there is recycling of any of the unreacted components will depend, inter alia, upon the extent of conversion, the economic value of the reactant, the ease with which the unreacted materials are separated from the reaction products, and so forth.

The following examples merely illustrate our invention, which is not to be limited thereto or circumscribed thereby in any way.

EXAMPLE 1

Preparation of Ultra-Low Sodium Silica-Alumina

The following procedure is typical of that used to prepard silica-alumninas with a low sodium content and utilizes an ammonium nitrate wash of the calcined base. A 75:25 silica-alumina was washed with a 15 weight percent aqueous ammonium nitrate solution in an amount such that the total weight of ammonium nitrate was equal to the weight of the silica-alumina being washed. The wash solution (as well as the rinse) temperature was 88° C. (190° F.) and was pumped upflow through a bed of silica-alumina at a linear velocity of 1 cm/min. for 5 hours with recycle of the used wash solution. The silica-alumina was contained in a column of 1" diameter and had a volume of approximately 165 cc. After the wash was complete, the silica-alumina was rinsed with 3–4 volumes of deionized water at 190° F. pumped upflow at a linear velocity of 1 cm/min. The washed catalyst was oven dried at 149° C. (300° F.) for 4 hours. For one sample the wash solution was 1 normal hydrochloric acid instead of 15% ammonium nitrate. Table 1 summarizes the sodium content of the silica-alumina before treatment and after being washed and rinsed as described.

TABLE 1

| SAMPLE | Sodium Content of Silica-Alumina NH₄NO₃ WASH EXPERIMENTS SAMPLE TREATMENT | Na, wt % |
|---|---|---|
| A | NONE | 0.20 |
| B | Standard Wash | 0.03 |
| C | Standard Wash | 0.03 |
| D | Standard Wash | 0.04 |
| E | Standard Wash except 20 wt % NH₄NO₃ and 10 cm/min wash and rinse velocity | 0.03 |
| F | Standard wash except 1.0 N HCl | 0.01 |

These results show that it is possible to routinely obtain a sodium content of 0.03 weight percent on a silica-alumina using the described procedure. Where the wash solution is one normal hydrochloric acid instead of the standard ammonium nitrate an even lower sodium value of 0.01 weight percent can be obtained, but at these conditions there is also some dissolution of alumina.

EXAMPLE 2

Effect of Sodium Content on Catalyst Stability

Catalyst performance was evaluated in a standard detergent alkylation of benzene. All pilot plant tests were conducted in a fixed bed reactor operating at 135° C., a benzene to olefin feed molar ratio of 25, a liquid hourly space velocity of 2.0 hr$^{-1}$, and a pressure of 500 psig. The fresh feed was obtained from a commercial alkylation unit. The composition given in Table 2 is typical of such feedstocks. Olefin conversion was monitored by gas chromatic graphic analysis of the product. The n-paraffins were used as an internal standard for calculating conversion at each carbon number.

TABLE 2

| Commercial Alkylation Feedstock Composition | |
|---|---|
| Linear Paraffins and olefins | weight percent |
| C-10 | 13.7 |
| C-10= | 1.7 |
| C-11 | 26.1 |
| C-11= | 3.5 |
| C-12 | 22.2 |
| C-12= | 3.3 |
| C-13 | 14.9 |
| C-13= | 2.8 |
| C-14 | 5.1 |
| C-14= | 0.1 |
| Aromatics | 5.2 |
| Others | 1.4 |

The catalysts whose performance was tested were 75:25 silica-alumina having an ABD in the range 0.63–0.69 g/cc and a BET surface area of 327–346 m²/g which were fluorided. The results are tabulated in Table 3.

TABLE 3

| THE EFFECT OF SODIUM CONCENTRATION ON CATALYST PERFORMANCE | | | | | | |
|---|---|---|---|---|---|---|
| Catalyst | G | H | I | J | K | L |
| F, wt % | 2.3 | 3.0 | 2.9 | 2.8 | 2.6 | 2.7 |
| Na, wt % | 0.05 | 0.09 | 0.21 | 0.04 | 0.17 | 0.29 |
| Life (>99 wt % Conversion), hr. | 48 | 52 | 30 | 62 | 36 | 28 |
| Linearity, wt % | 92.2 | 92.5 | 92.6 | 92.5 | 92.5 | 92.5 |
| Selectivity, wt % | 90.3 | 89.0 | 89.5 | 89 | 89 | 89 |

These data clearly show the substantial effects accruing from lowering the sodium content of silica-aluminas on catalyst lifetime. Thus, catalyst L with a sodium content of 0.29 weight percent has a lifetime (i.e., the number of hours it is capable of at least 99% conversion of olefins) of only 28 hours. Reducing the sodium content to 0.04 weight percent increases the lifetime to 62 hours. There appears to be no substantial difference among the catalysts in linearity, which is to be expected if linearity is primarily a function of temperature. Variation in selectivity among the catalysts is relatively minor.

EXAMPLE 3

Effects of Size and Sodium Content

A sample of 75:25 silica-alumina was oil dropped so as to afford 1/32" diameter spheres. All the spheres fell through a #20 screen (0.0331 inches, 0.841 mm) and on to a #25 screen (0.0278 inches, 0.707 mm). The silica-alumina was treated as described in Example 1 to afford a sample of low sodium silica-alumina which was tested for its performance as described in Example 2. Table 4 summarizes the results obtained with this silica-alumina as a catalyst for detergent alkylation at 120° C. compared with another, similar silica-alumina catalyst but having a 1/16" diameter.

TABLE 4

| THE EFFECT OF SIZE ON CATALYST PERFORMANCE | | |
|---|---|---|
| Catalyst | M | N |
| ABD, g/cc | 0.53 | 0.50 |
| Na, wt % | 0.04 | 0.02 |
| Diameter, in. | 1/16 | 1/32 |
| BET Surface Area, m$_2$/g | 339 | 371 |
| Life (>99 wt % conversion), hr. | 0 | 48 |
| Linearity, wt % | 93 | 94 |
| Selectivity, wt % | 85 | 89.5 |

The foregoing data clearly show that whereas the small 1/32" spheres have a substantial lifetime even at 120° C. under test conditions, the 1/16" catalyst had essentially no stability. Thus, the combination of a low sodium silica-alumina with small particle diameter affords a catalyst which is operationally suitable for use at 120° C., thereby affording a product with 94% linearity.

What is claimed is:

1. A process for alkylating benzene with one or more linear monoolefins in an alkylation feedstock, said monoolefins having from 6 up to about 20 carbon atoms, with at least 98% conversion of monoolefins, at least 85% selectivity of monoolefin conversion to monoalkylbenzenes, and with at least 90% linearity with respect to monoalkylbenzene formation comprising reacting benzene with the linear monoolefins in the feedstock at alkylating conditions and in the presence of a catalyst, said feedstock containing at least one linear monoolefin, said alkylating conditions including reacting from about 5 to about 30 molar proportions of total benzene for each molar proportion of total linear monoolefins at a temperature from about 60° C. to about 175° C. and a pressure from about 200 to about 1000 psig, where the catalyst is a silica-alumina having a silica:alumina weight ratio of from about 1:1 to about 19:1 and has a sodium content of less than about 0.1 weight percent.

2. The process of claim 1 where the sodium content is no more than about 0.05 weight percent.

3. The process of claim 1 where the sodium content is no more than about 0.03 weight percent.

4. The process of claim 1 where the molar ratio of benzene to linear monoolefins is from about 8 to about 20.

5. The process of claim 1 where the temperature is from about 70° to about 150° C.

6. The process of claim 5 where the temperature is from about 80° to about 135° C.

7. The process of claim 1 where the monoolefins have from about 8 to about 16 carbon atoms.

8. The process of claim 7 where the monoolefins have from about 10 to about 14 carbon atoms.

9. The process of claim 1 where the catalyst has a silica to alumina weight ratio of from 67:33 to about 19:1.

10. The process of claim 1 further characterized in that the catalyst contains from about 1 up to about 6 weight percent fluorine.

11. The process of claim 1 where the catalyst contains from 1.5 to about 3.5 weight percent fluorine.

12. The process of claim 1 further characterized in that the catalyst is in the form of spherical particles whose diameter is no more than about 1/16 inch.

13. The process of claim 12 where the catalyst is in the form of spherical particles whose diameter is no more than about 1/32 inch.

14. A process for the production of a biodegradable detergent alkylbenzene sulfonate which comprises: alkylating benzene with at least one linear monoolefin containing from 6 to about 20 carbon atoms at alkylating conditions in an alkylation zone in the presence of a catalytic composite to selectively form monoalkylated benzenes, said catalytic composite being a silica-alumina having a silica:alumina weight ratio of from about 1:1 to about 19:1 and containing less than about 0.1 weight percent sodium; sulfonating the monoalkylated benzenes in a sulfonation zone with a sulfonating agent at sulfonation conditions to form sulfonic acids of the monoalkylated benzenes; and reacting said sulfonic acids with an aqueous solution of an alkali metal base to form the monoalkylbenzene alkali metal sulfonate.

15. The process of claim 14 where the sodium content is no more than about 0.05 weight percent.

16. The process of claim 15 where the sodium content is no more than about 0.03 weight percent.

17. The process as set forth in claim 14 in which said alkylation conditions include a temperature in the range of from about 60° to about 175° C., a pressure in the range of from about 200 to about 1,000 pounds per square inch gauge, and from about 5 to about 30 molar proportions of benzene for each molar proportion of linear monoolefin.

18. The process of claim 14 where the molar ratio of benzene to linear monoolefins is from about 8 to about 20.

19. The process of claim 14 where the temperature is from about 70° up to about 150° C.

20. The process of claim 19 where the temperature is from about 80° up to about 135° C.

21. The process of claim 14 where each monoolefin has from about 8 to about 16 carbon atoms.

22. The process of claim 21 where each monoolefin has from about 10 to about 14 carbon atoms.

23. The process of claim 14 where the catalyst has a silica to alumina weight ratio of from 67:33 to about 19:1.

24. The process of claim 14 further characterized in that the catalyst contains from about 1 up to about 6 weight percent fluorine.

25. The process of claim 14 where the catalyst contains from 1.5 to about 3.5 weight percent fluoride.

26. A process of alkylating an alkylatable aromatic compound with an alkylating agent comprising reacting the alkylatable aromatic compound with the alkylating agent under alkylating conditions in the presence of an alkylation catalyst comprising a silica-alumina having a silica:alumina weight ratio of from about 1:1 up to about 19:1 and having a sodium content of less than about 0.1 weight percent.

27. The process of claim 26 where the alkylatable aromatic compound is selected from the group consisting of benzene, naphthalene, anthracene, phenanthrene, and benzene, naphthalene, anthracene, and phenanthrene bearing at least one substituent selected from the group consisting of alkyl, hydroxy, alkoxy, phenyl, and phenylalkyl, where each alkyl and alkoxy group contains from 1 up to about 20 carbon atoms.

28. The process of claim 27 where the alkylatable aromatic compound is benzene.

29. The process of claim 27 where the alkylatable aromatic compound is toluene.

30. The process of claim 27 where the alkylatable aromatic compound is a hydroxybenzene.

31. The process of claim 27 where the alkylatable aromatic compound is an alkoxybenzene.

32. The process of claim 27 where the alkylating agent is an olefin, an alcohol, or an alkyl halide containing from 1 up to about 20 carbon atoms.

33. The process of claim 26 further characterized in that the catalyst contains from about 1 up to about 6 weight percent fluorine.

34. The process of claim 26 where alkylating conditions include a temperature from about 60° up to about 400° C.

35. The process of claim 34 where the temperature is from about 100° up to about 225° C.

* * * * *